United States Patent [19]

Namba et al.

[11] 4,430,306
[45] Feb. 7, 1984

[54] OXYGEN RECYCLE TYPE OZONIZING APPARATUS

[75] Inventors: Keisuke Namba; Masaaki Tanaka; Takanori Ueno; Norikazu Tabata, all of Amagasaki, Japan

[73] Assignee: Mitsubishi Denki Kabushiki Kaisha, Tokyo, Japan

[21] Appl. No.: 326,760

[22] Filed: Dec. 2, 1981

Related U.S. Application Data

[63] Continuation of Ser. No. 152,318, May 22, 1980, abandoned.

[30] Foreign Application Priority Data

May 29, 1979 [JP] Japan .................. 54-66549

[51] Int. Cl.$^3$ .................. A61L 2/20; B01D 53/04; C02F 1/50; C02F 1/78
[52] U.S. Cl. .................. 422/292; 55/30; 55/31; 55/75; 210/192; 210/760; 422/31; 422/186.05; 422/186.07; 422/186.09
[58] Field of Search .................. 422/29, 31, 32, 292, 422/186.05, 186.07, 186.09; 210/192, 760; 250/532, 538; 55/30, 31, 75

[56] References Cited

U.S. PATENT DOCUMENTS

| | | | |
|---|---|---|---|
| 2,539,005 | 1/1951 | Berg | 55/79 X |
| 2,616,515 | 11/1952 | Berg | 55/79 X |
| 2,630,877 | 3/1953 | Berg | 55/79 X |
| 3,748,262 | 7/1973 | Lee et al. | 210/192 X |
| 3,856,671 | 12/1974 | Lee et al. | 210/192 X |
| 4,100,421 | 7/1978 | Tabata et al. | 55/31 X |
| 4,319,892 | 3/1982 | Waghorne et al. | 55/75 X |

Primary Examiner—Barry S. Richman
Attorney, Agent, or Firm—Oblon, Fisher, Spivak, McClelland & Maier

[57] ABSTRACT

An ozonized oxygen fed from an ozonizer is passed to a reaction tower to treat an object material. In recovering non-reacted oxygen from the reaction tower to reuse in the ozonizer, zeolite is used as an adsorbent to remove impurities contained in the recovered oxygen, such as water, volatile organic materials and $CO_2$ gas so that a raw material oxygen without containing any impurity is fed to the ozonizer to increase the ozonizing efficiency.

1 Claim, 5 Drawing Figures

OXYGEN RECYCLE TYPE OZONIZING APPARATUS

This is a continuation of application Ser. No. 152,318, filed May 22, 1980 now abandoned.

BACKGROUND OF THE INVENTION

1. Field of the Invention

The present invention relates to an improved oxygen recycle type ozonizing apparatus.

2. Description of the Prior Arts

Ozone is used as an oxidizing agent in a water treatment or a production process because its strong oxidizing function and sterilizing function. It has been known that more than two times the amount of ozone is obtained by using oxygen gas as a raw material instead of air in an ozonizer thereby reducing a substantive power comsumption of the ozonizer. However, in such case, an oxygen recycle system is required for using the oxygen gas as a raw material effectively.

FIG. 1 is a diagram of an embodiment of the conventional water treating apparatus using ozone which has an oxygen recycle system.

In FIG. 1, the reference numeral (1) designates an ozonizer, (2) designates a reaction tower, (3) designates a blower, (4) designates a cooling and moisture-removing device, (5) designates an air-diffusing plate, (6) designates a container for oxygen gas and (10) designates an adsorption type gas drier.

The operation of the conventional apparatus will be described.

Oxygen gas as the raw material is fed from the container (6) and is supplied to the ozonizer (1) in which an ozonized oxygen having an ozone concentration of several percents is produced and the resulting ozonized oxygen is consumed by the discharging in water as fine bubbles from the orifices of the air-diffusing plate (5) at the bottom of the reaction tower (2). During the bubbling, most of the oxygen rises to water surface to exit from the top of the reaction tower (2) whereas a small portion of oxygen is dissolved in the water and is discharged with the water. The discharged water is sucked and compressed by the blower (3) and is cooled at about 5° C. by the cooling and moisture-removing device (4) to which a cooled brine is fed from a refrigerator (not shown) to condense water component contained in the gas and the resulting water is removed as a drainage. The gas from the cooling and moisture-removing device (4) is fed to the adsorption type gas drier (10) wherein the gas is dried to give the dew point of lower than $-40°$ C. and then is recycled to the container (6) as the oxygen gas source. The recycle system of this type is referred to as an oxygen recycle system. An amount of oxygen equal to a sum of the ozonized oxygen and the oxygen dissolved in the water to be discharged is added as oxygen for supply.

The adsorption type gas drier (10) usually comprises two or more adsorption towers (11), (12) in which silica gel or an activated alumina is packed as an adsorbent for removing water. In the case of the two tower arrangement as shown in FIG. 1, when one tower operates for the adsorbing and removing of water, the other tower operates for the regenerating of the adsorbent by feeding hot air from a heater (60) for the gas. After the predetermined time, switching valves (21), (22), (31), (32), (41), (42), (51) and (52) are switched to change the operation for one to the other. Thus, the moisture-removing and the regenerating operations are repeated alternately for the two adsorption towers to dry the discharged oxygen continuously.

However, in the conventional oxygen recycle type ozonizing apparatus, the decrease of ozonizing efficiency is found depending upon the progress of the operating time. In the study of the cause, the presence of a large amount of $CO_2$ gas and a small amount of volatile organic materials are found in the oxygen returned from the adsorption gas drier. That is, in the conventional apparatus having the reaction towers in the recycle system, the volatile organic materials or $CO_2$ gas which are contained in the water by the vaporization during the exposing of the treated water to air or which is produced as low molecular organic materials as a result of the reaction of the organic materials dissolved in the water with ozone and volatile organic materials contained in non-treated water are involved in the discharged oxygen. Accordingly, the volatile organic materials can not be satisfactorily removed and the adsorbing and removing of the $CO_2$ gas contained as a main component of impurity is not substantially attained in the conventional adsorption type gas drier (10) using silica gel or activated alumina as the adsorbent to remove water; thus the ozonizing efficiency decreases.

It is possible to remove a sufficient amount of the $CO_2$ gas and the volatile organic materials by increasing a volume of the adsorbent. However, this requires a large capacity of the apparatus and the oxygen filled in the adsorption tower should be discharged depending upon the capacity of the apparatus thereby causing a discharge loss. This is inadvantageous from the economical viewpoint.

The inventors have studied and found that when the gas in the oxygen recycle system comprises 90 to 95% of oxygen and 5 to 10% of nitrogen, a superior ozonizing effect can be obtained by using a $CO_2$ gas concentration of 1 to 2% in comparison with that of zero.

SUMMARY OF THE INVENTION

It is an object of the present invention to remove a sufficient amount of $CO_2$ gas and volatile organic materials contained in the discharged gas recovered from a reaction tower.

It is another object of the invention to remove the $CO_2$ gas and volatile organic materials without increasing the capacity of an apparatus.

It is further object of the invention to adjust especially the adsorbing rate of the $CO_2$ gas to permit the presence of a slight amount of $CO_2$ gas in oxygen gas fed to an ozonizer thereby increasing ozonizing efficiency.

It is the other object of the invention to attain the reuse of the adsorbent by a small energy by using the adsorbent for removing especially the $CO_2$ gas and the volatile organic materials and the adsorbent for removing especially water.

The foregoing and other objects of the present invention have been attained by providing an oxygen recycle type ozonizing apparatus for feeding an ozonized oxygen to a liquid or solid object part including organic materials to react them and treating gas discharged after the reaction to reuse it as oxygen gas to be ozonized, which is characterized by comprising an ozonizing means for producing ozonized oxygen; a reacting means for reacting the object to be treated with the ozonized oxygen produced in the ozonizing means; and a recovering means for recovering the gas discharged from the reacting means to adsorb and remove impurities in the discharged gas and to feed the gas to the ozonizing means, said recovering means holding Ca A type or X type zeolite as an adsorbent to adsorb and remove the impurities.

BRIEF DESCRIPTION OF THE DRAWINGS

The same reference numerals designates the same or corresponding parts throughout several figures.

DETAILED DESCRIPTION OF THE PREFERRED EMBODIMENTS

Figure 1:
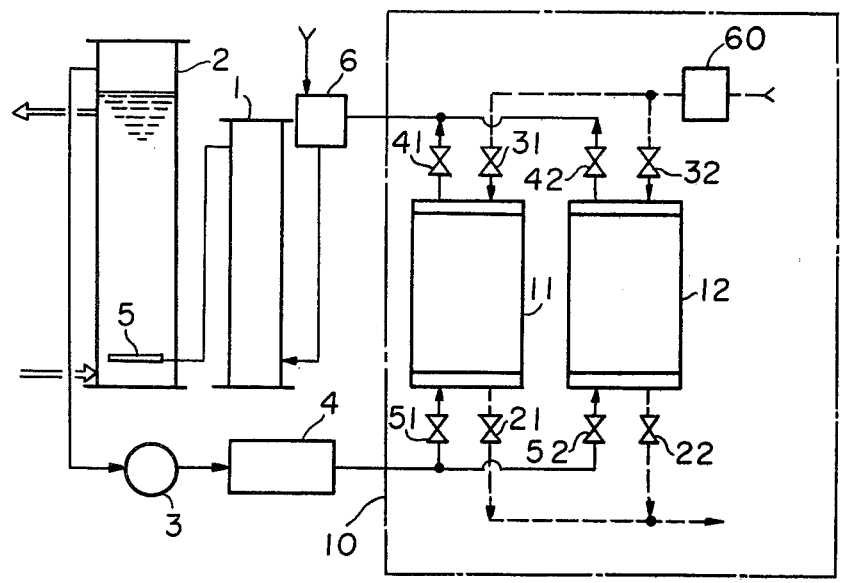
FIG. 1 is a diagram of an embodiment of the conventional oxygen recycle type ozonizing apparatus.
Figure 2:
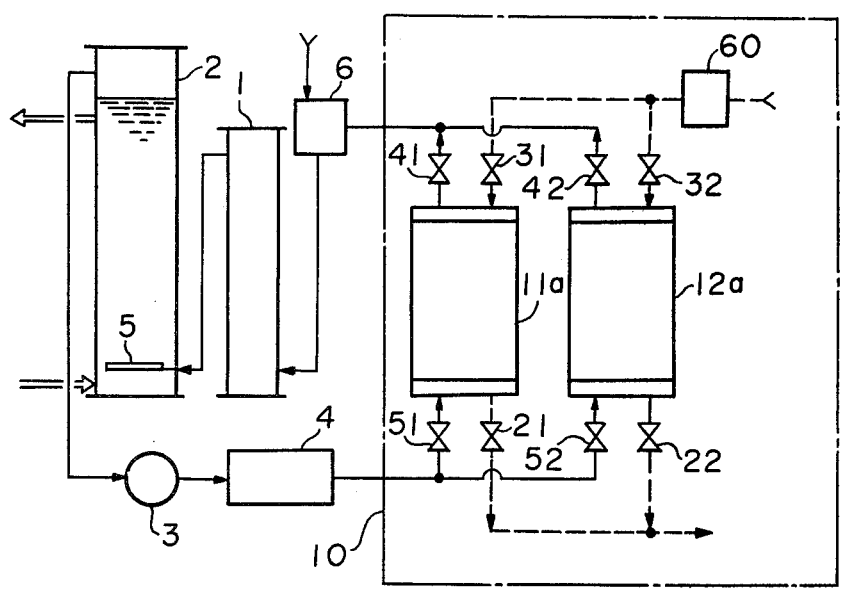
FIG. 2 is a diagram of an embodiment of the ozonizing apparatus of the present invention.

In FIG. 2, the reference numeral (1) designates an ozonizer, (2) designates a reaction tower, (3) designates a blower, (4) designates a cooling and moisture-removing device, (5) designates a reaction tower, (6) designates a container for a raw material gas and (10) designates an adsorption type gas drier. This arrangement and structure is the same as that of FIG. 1 except an adsorbent held in adsorption towers (11a) and (12a) of the drier (10). These adsorbent towers (11a), (12a) are packed with Ca A type zeolite or X type zeolite (molecular sieves 5A or 13X) as the adsorbent.

The operation of the ozonizing apparatus of this embodiment is basically the same as that of FIG. 1 except that the adsorption and the removal of volatile organic impurities and $CO_2$ gas contained in oxygen discharged from the reaction tower (2) is carried out as water is adsorbed and removed. The adsorbing function of the adsorbent specified above decreases in order of water, volatile organic materials and $CO_2$ gas. Accordingly, it is easy to make the condition, by adjusting an amount of the adsorbent, that the water and the volatile organic materials greatly affecting to the ozonizing efficiency are substantially removed and a small amount of $CO_2$ gas is passed to feed to the ozonizer (1). That is, when $CO_2$ gas is contained in the recycle system to decrease the ozonizing efficiency, the amount of the adsorbent is increased to remove $CO_2$ gas much, whereas the presence of a slight amount of $CO_2$ gas is desired to improve the ozonizing efficiency, the amount of the adsorbent is reduced to pass $CO_2$ gas at constant and in the desirable concentration.

As described above, in this embodiment, the Ca A type or X type zeolite is used as the adsorbent in the adsorption type gas drier of the oxygen recycle type ozonizing apparatus. Accordingly, the decrease of the ozonizing efficiency is certainly prevented and moreover, the ozonizing efficiency is further improved by passing a small amount of $CO_2$ gas.

Figure 4:
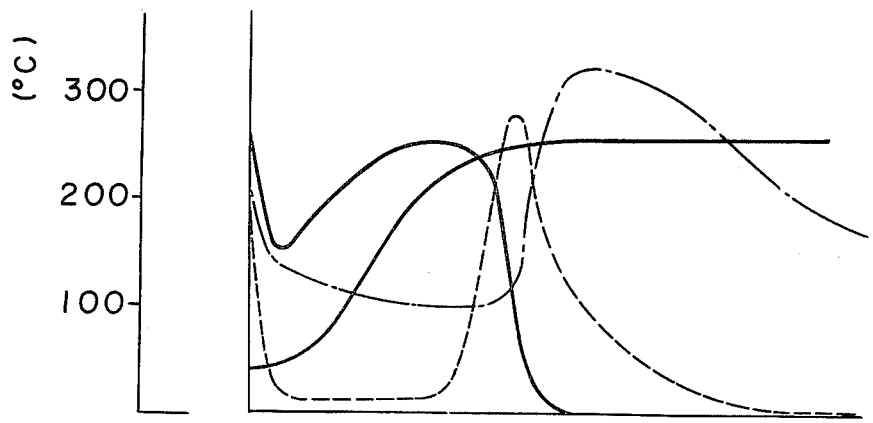
FIG. 4 is a characteristic curve of the separation of adsorbed gas during the regeneration of an adsorbent in the embodiment shown in FIG. 2.

FIG. 4 is a diagram showing each component in the oxygen discharged from the adsorbent tower in the regenerating step of the adsorbent in the embodiment. In this embodiment, the temperature in the regeneration step is 250° C. from the economical viewpoint. However, the temperature can be elevated up to 450° C. and the desorbing of the organic material is accelerated depending upon the increase of the temperature. The reason for providing the upper limit of 450° C. is that the sintering of the synthetic zeolite is initiated in near this point and the crystal structure of the synthetic zeolite is changed at the excess of the point resulting in the decrease of the adsorbing function.

When the temperature in the regenerating step is too low, the desorbing of the water and the organic materials become slow or a satisfactory desorbing can not be carried out. Accordingly, the temperature in the regenerating step should be determined in an economical sense taking into account of energy required for the regeneration, the regeneration time etc.

Figure 3:
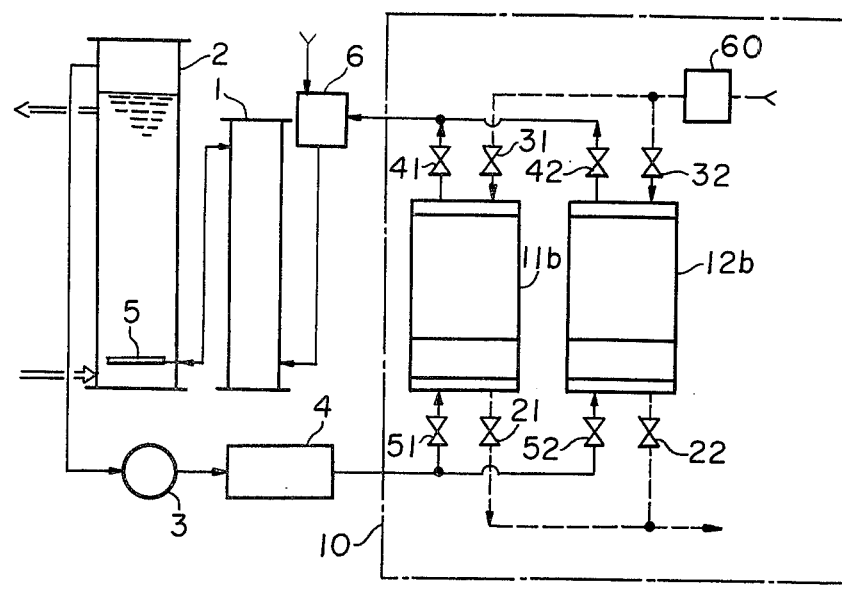
FIG. 3 is a diagram of another embodiment of the ozonizing apparatus of the present invention.

FIG. 3 is a schematic view of another embodiment of the present invention. The Ca A type or X type zeolite is packed in the adsorbent tower (11b) and (12b) and an activated alumina or silica gel is placed at the upstream side (in the meaning of the adsorbing step) of the Ca A type or X type zeolite so as to form two layers. The structure and the operation of the embodiment as shown in FIG. 3 are the same as those of FIG. 2 except the structure described above. Accordingly, in FIG. 3, the same parts as those of FIG. 2 is shown by the same reference numerals to omit the description. Ca A type or X type zeolite is an ideal adsorbent in adsorbing and removing water, volatile organic materials and $CO_2$ gas as described. However, the regeneration of the adsorbent can not be sufficiently attained unless a sufficiently heated air is used for the desorption of the water. However, the regeneration of the adsorbent is performed at lower temperature by placing the activated alumina or the silica gel at the upstream of the zeolite to adsorb the water. When the regeneration temperature is not low, the regeneration is finished in a short time.

Figure 5:
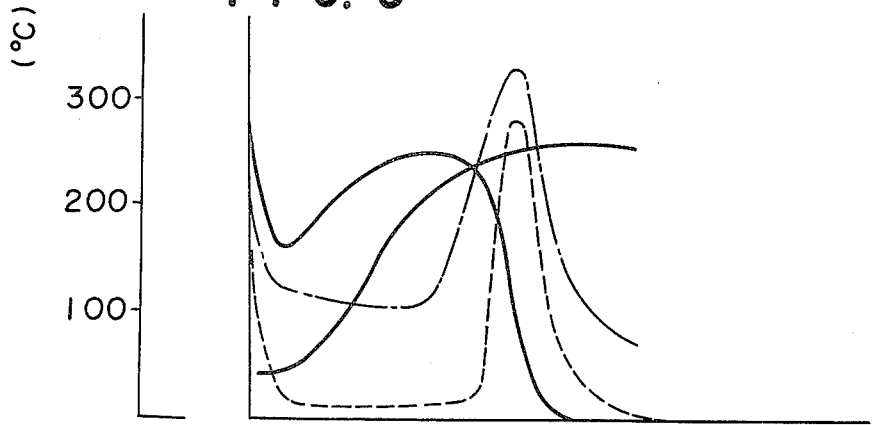
FIG. 5 is a characteristic curve of the separation of the adsorbed gas during the regeneration of the adsorbent in the embodiment of FIG. 3.

The embodiment shown in FIG. 2 overcomes the difficulty in the desorption of water and reduces an expense of energy required in the regenerating of the adsorbent and the regenerating time. The merit can be understood from the comparison of the characteristic diagram of FIG. 5 with that of FIG. 4.

Even in the embodiment shown in FIG. 3, the selectivity of the water, the volatile organic materials and $CO_2$ gas in the adsorbing step and the ozonizing efficiency can be maintained the same as those of FIG. 2.

The present invention is applicable to not only the water treatment but also to an ozonizing apparatus for reacting ozone to a solid or liquid object part containing organic materials.

Ad described above, the present invention provides an oxygen recycle type ozonizing apparatus employing Ca A type or X type zeolite as an adsorbent for discharged oxygen to improve the selectivity for water, volatile organic materials and $CO_2$ gas thereby increasing the ozonizing efficiency.

What is claimed is:

1. An oxygen recycled type ozonizing apparatus for feeding ozonized oxygen to a liquid or solid object part containing organic materials to be treated with said ozonized oxygen and subsequently treating the gas discharge after the reaction to reuse it as a source of oxygen for producing ozone, comprising:

a source of oxygen with said source producing oxygen which is essentially substantially pure oxygen;
an ozonizing means for producing ozonized oxygen from said substantially pure oxygen;

a reacting means for reacting the liquid or the object to be treated with the ozonized oxygen produced in said ozonizing means;

a temperature-swing recovery means connected to said reacting means for recovering the discharged gas of the reacting means to adsorb and remove the impurities contained in the discharged gas and to feed the gas to resupply said source of substantially pure oxygen which is, in turn, fed to said ozonizing means, wherein said recovery means holds a first adsorbent of one of silica gel and activated aluminum for adsorbing mainly water in the discharged gas and a second adsorbent of one of Ca A type and X type zeolite for adsorbing mainly volatile organic materials and $CO_2$ gas in said discharge gas, said first adsorbant being located upstream of said second adsorbant, and heater means for heating said second adsorbant to a temperature of 250° C. in order to carry out said adsorbing operation.

* * * * *